(12) United States Patent
Spinnler et al.

(10) Patent No.: US 9,192,290 B2
(45) Date of Patent: Nov. 24, 2015

(54) ILLUMINATION APPARATUS FOR AN IMAGE SENSING MEANS AT THE DISTAL END OF AN ENDOSCOPE

(75) Inventors: Klaus Spinnler, Erlangen (DE);
Cornelia Arnold, Renthendorf (DE);
Andreas Kuleschow, Oberasbach (DE);
Stephan Rupp, Nuremberg (DE);
Thomas Wittenberg, Erlangen (DE);
Robert Couronné, Erlangen (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 1550 days.

(21) Appl. No.: 12/021,481

(22) Filed: Jan. 29, 2008

(65) Prior Publication Data
US 2008/0183043 A1 Jul. 31, 2008

(30) Foreign Application Priority Data

Jan. 31, 2007 (DE) .......................... 10 2007 005 464
Mar. 30, 2007 (DE) .......................... 10 2007 015 492

(51) Int. Cl.
*A61B 1/06* (2006.01)
*H04N 5/225* (2006.01)

(52) U.S. Cl.
CPC ............. *A61B 1/0676* (2013.01); *A61B 1/0684* (2013.01); *H04N 5/2256* (2013.01); *H04N 2005/2255* (2013.01)

(58) Field of Classification Search
CPC ...... A61B 1/06; A61B 1/0607; A61B 1/0615; A61B 1/0623; A61B 1/0661; A61B 1/0676; A61B 1/0684; A61B 1/0692; A61B 1/00163; A61B 1/00174; A61B 1/00177; A61B 1/00179; A61B 1/00181
USPC .......... 600/160, 175, 178–180, 170, 171, 176
See application file for complete search history.

(56) References Cited

U.S. PATENT DOCUMENTS 5,538,497 A * 7/1996 Hori .............................. 600/182
6,333,826 B1 * 12/2001 Charles ........................ 359/725
(Continued)

FOREIGN PATENT DOCUMENTS

JP 58-29439 A 2/1983
JP 61-267725 A 11/1986
(Continued)

OTHER PUBLICATIONS

English translation of Official Communication issued in corresponding Japanese Patent Application No. 2008-019437, mailed on May 22, 2012.

*Primary Examiner* — Anhtuan T Nguyen
*Assistant Examiner* — William Chou
(74) *Attorney, Agent, or Firm* — Keating & Bennett, LLP

(57) ABSTRACT

An illumination apparatus for an image sensor at the distal end of an endoscope includes an illumination carrier and a plurality of micro LEDs each including a main surface from which the emission is made, with a maximum lateral dilatation of less than 500 μm. The illumination carrier is associated with the distal end of the endoscope, and the plurality of micro LEDs are arranged on the illumination carrier such that with electrical excitation, the environment of the distal end of the endoscope is at least in some portions illuminated.

33 Claims, 14 Drawing Sheets

(56) References Cited

U.S. PATENT DOCUMENTS

| | | |
|---|---|---|
| 6,410,997 B1 | 6/2002 | Sjursen et al. |
| 6,734,893 B1 | 5/2004 | Hess et al. |
| 7,909,756 B2 * | 3/2011 | Hoeg et al. .................... 600/173 |
| 7,922,655 B2 * | 4/2011 | Yasushi et al. ................. 600/173 |
| 2002/0193664 A1 | 12/2002 | Ross et al. |
| 2004/0249247 A1 * | 12/2004 | Iddan ............................ 600/170 |
| 2005/0049462 A1 * | 3/2005 | Kanazawa .................... 600/170 |
| 2005/0127375 A1 | 6/2005 | Erchak et al. |
| 2006/0058584 A1 * | 3/2006 | Hirata ........................... 600/179 |
| 2006/0063976 A1 * | 3/2006 | Aizenfeld et al. ............. 600/179 |
| 2006/0069309 A1 | 3/2006 | Ono |
| 2006/0069313 A1 * | 3/2006 | Couvillon et al. ............ 600/179 |
| 2006/0069314 A1 * | 3/2006 | Farr .............................. 600/179 |
| 2006/0071225 A1 | 4/2006 | Beeson et al. |
| 2006/0149129 A1 * | 7/2006 | Watts et al. ................... 600/113 |
| 2006/0184214 A1 * | 8/2006 | McDaniel ....................... 607/89 |
| 2006/0256431 A1 | 11/2006 | Hoeg et al. |
| 2007/0049794 A1 * | 3/2007 | Glassenberg et al. ......... 600/109 |
| 2007/0073109 A1 | 3/2007 | Irion |
| 2007/0185384 A1 * | 8/2007 | Bayer et al. ................... 600/129 |
| 2008/0294009 A1 * | 11/2008 | Long .............................. 600/179 |
| 2010/0137682 A1 * | 6/2010 | Doguchi et al. .............. 600/109 |
| 2011/0241574 A1 * | 10/2011 | Erchak et al. ................ 315/312 |

FOREIGN PATENT DOCUMENTS

| | | |
|---|---|---|
| JP | 05-79676 A | 3/1993 |
| JP | 05-267697 A | 10/1993 |
| JP | 2002-51971 A | 2/2002 |
| JP | 2002-521947 A | 7/2002 |
| JP | 2002-224032 A | 8/2002 |
| JP | 2003-116783 A | 4/2003 |
| JP | 2004-133108 A | 4/2004 |
| JP | 2004-297630 A | 10/2004 |
| WO | 95/15060 A1 | 6/1995 |
| WO | 01/73859 A1 | 10/2001 |
| WO | 02/059983 A1 | 8/2002 |

* cited by examiner (B)

(C)

(D)

ILLUMINATION APPARATUS FOR AN IMAGE SENSING MEANS AT THE DISTAL END OF AN ENDOSCOPE

CROSS-REFERENCE TO RELATED APPLICATIONS

This application claims priority from German Patent Application No. 102007015492.7, which was filed on Mar. 30, 2007, and is incorporated herein in its entirety by reference, and German Patent Application No. 102007005464.7, which was filed on Jan. 31, 2007, and is incorporated herein in its entirety by reference.

TECHNICAL FIELD

The present invention relates to an illumination apparatus for an image sensing means and a method for operating an illumination apparatus and, in particular, to an illumination apparatus for an image sensing means at the distal end of an endoscope.

BACKGROUND

Endoscopy is an important, non-destructive inspection method for examining, in medicine and technology, small cavities which in general are difficult to access. In an endoscope, a distal end is distinguished from a proximal end. The distal end refers to the "remote" end of an endoscope which is introduced into an object for observing internal structures, while the proximal end basically remains outside the examined cavity. In this process, viewing the image is made through the proximal end, e.g. by means of a look into an ocular or by connecting a camera. While in the past the endoscopic inspection has been performed manually by the human examiner or doctor, is has been tried in recent time, in the course of the development of automatic visual examination systems, to increasingly deploy automated endoscopic examination systems.

Especially in the area of hydraulic or pneumatic devices (e.g. brake cylinders, control elements etc.) with functional bore surfaces, there are high quality demands often necessitating full control of the entire production. This examination offers a high rationalization potential if corresponding endoscopic examination automatics are available.

Substantially, two basic approaches for illuminating cavities during an endoscopic examination thereof are known.

On the one hand, miniature lamps attached to the distal end of the endoscope, for example, serve for illuminating the sensed scene or environment. The relatively large design, even of miniature lamps, which makes the deployment in very small, thin endoscopes impossible, is one disadvantage. The relatively high portion of thermal emission is also problematical in this technique. In lamps with a higher power, this quickly leads to an inacceptably high heat input into the object examined.

For this reason, the technique predominantly used nowadays is a fiber-optically input cold light illumination. In this context, an efficient light source (e.g. a halogen lamp or an arc lamp) is located outside the cavity. The light output is gathered by means of optics (mirrors, condensers) and transferred to the tip of the endoscope by fiber optic light guides, and there, it exits at the end of the light guide fibers. Minimizing the transferred infrared portion is achieved by suitable infrared blocking filters. The light such filtered is also referred to as "cold light". The disadvantages of this technique are the illumination arrangement constructively fixedly predetermined by the light exit at the fiber bundle, the lossy light transmission as well as the efficient, expensive cold light sources necessitated.

In recent time, the external cold light sources have also been replaced by external LED light sources with high-efficiency LEDs (LED=light-emitting diode or a light-generating semiconductor element).

In most of the endoscopes available on the market, the integrated fiber optic illumination is implemented in a dark field arrangement. Due to the avoidance of shiny and dazzling effects, this kind of illumination has proved to be especially suitable for the human viewer.

In the dark field arrangement, a light-guiding fiber bundle is attached to the shaft of the endoscope, so that the light exit is close to or coaxially around the distal objective. In this context, the light exit at the fiber bundle is fixedly predetermined by the construction of the device, so that apart from the total intensity of the illumination, no further illumination parameters may be influenced by regulation of the external light source.

In the automatic technical endoscopy, the inspection of a cavity (a bore) is made without human intervention by an image processing system motor-driving an endoscope with a video camera and an accordingly suitable illumination into and out of the cavity for an automatic image gain. The images thus gained are automatically evaluated by means of image processing algorithms. Thus, an evaluation of the cavity (or device) examined is determined, which in turn may be used for sorting out defective parts.

In many devices, the dark field illumination commonly integrated by endoscope manufacturers has proved to be not quite suitable and a part field illumination has proved to be advantageous for the automated examination by means of image processing algorithms. Using the bright field illumination, several arrangements are known in the endoscopic bore examination. For through bores with two openings, the introduction of the endoscope is made from one side of the bore, and the introduction of the illumination, e.g. in the form of a light finger, is made from the other side. A light finger is a rod or "finger"-shaped rigid or flexible apparatus at the end of which light exits by means of a fiber optic light guide, for example. The image sensing is made by a simultaneous movement of the endoscope and the illumination through the bore with a constant distance, so that a constant bright field arrangement is guaranteed during the entire image capture, considering the bore diameter, the image angle of the optics etc.

This is not possible with sack bores having only one opening. Here, the light source may be mounted to a carrier in front of the distal endoscope tip and be introduced with the endoscope into the bore. In this process, the illumination is broadly emitting and directed to the optics, so that in turn a bright field illumination is achieved, considering the geometrical frame conditions. Another approach works with an "all-round backward look". In this context, the visual field is circumferentially turned over 360 degree to the side or backwards via a suitable mirror in front of the endoscope or a so-called Greguss lens. By an illumination attached around the shaft of the endoscope in a slightly offset manner, a bright field arrangement may in turn be achieved. Both approaches have in common the disadvantage that the base, or the last portion of the bore wall of the sack bore, cannot be sensed.

With respect to the endoscope illuminations deployed up to date, it should be noted, however, that the endoscopes nowadays available on the market substantially without any exception comprise illumination apparatuses whose mode of operation is optimized for viewing the endoscopic image by humans. Since in automated, endoscopic examination systems the images gained are not anymore sensed by the eye and are not anymore evaluated by humans, but are sensed and evaluated by cameras and image-processing pattern recognition algorithms in computers, other, new endoscope illuminations are needed to gain high-quality images for machine sensing (machine viewing). Thus, there is a particular need for illumination apparatuses for endoscopes which allow an optimized image gain in visual examination automates. Thereby, it should become possible to economically solve a large number of difficult examination tasks in devices with internal surfaces by means of automatic endoscopic visual examination systems, which up to date have not been feasible or have only been feasible with high personnel expenses and the associated costs.

SUMMARY

According to an embodiment, an illumination apparatus for an image sensing means at the distal end of an endoscope may have: an illumination carrier associated with the distal end of the endoscope, an array of micro LEDs each comprising a main surface comprising a maximum lateral dilatation of less than 500 µm from which the emission is made, and which are arranged on the illumination carrier such as to illuminate, with electrical excitation, at least some portions of an environment of the distal end of the endoscope, wherein the array of micro LEDs comprises a first and a second adjacent group of micro LEDs on a surface region of the illumination carrier, with a first and a second main emission direction which are different with respect to the surface region of the illumination carrier.

According to another embodiment, a method for operating an illumination apparatus for an image sensing means at a distal end of an endoscope, wherein the illuminator comprises an illumination carrier at the distal end with an array of micro LEDs, wherein the micro LEDs each comprise a main surface from which the emission is made and which comprises a maximum lateral dilatation of less than 500 µm, may have the steps of: illuminating at least one portion of an environment of the distal end of the endoscope by electrical excitation of the micro LEDs, wherein the array of micro LEDs comprises a first and a second adjacent group of micro LEDs on a surface region of the illumination carrier, with a first and a second main emission direction which are different with respect to the surface region of the illumination carrier.

According to another embodiment, a method for manufacturing an illumination apparatus for an image sensing means at the distal end of an endoscope may have the steps of: providing an array of micro LEDs on a carrier foil, wherein the micro LEDs each comprise a main surface comprising a maximum lateral dilatation of less than 500 µm from which the emission is made; and arranging the carrier foil on an illumination carrier which may be associated with the distal end of the endoscope to illuminate, with electrical excitation of the micro LEDs, an environment of the distal end of the endoscope at least in some portions.

Embodiments of the present invention describe an illumination apparatus for an image sensing means at the distal end of an endoscope comprising an illumination carrier arranged at the distal end of the endoscope and a plurality of micro LEDs, the micro LEDs each comprising a main surface from which emission is made, with a maximum lateral dilatation of less than 500 µm. The micro LEDs are arranged on the illumination carrier such that with an electrical excitation, the environment of the distal end of the endoscope is illuminated at least in some portions. In this context, the micro LEDs may be arranged in an array shape in particular, wherein the array may be designed as an area (2-dimensional), or as a line (1-dimensional) and the area or line may be curved or flush (e.g. sphere-, cylinder- or cuboid-shaped). The illumination carrier with the micro LEDs arranged in an array shape may also be arranged at an outer wall at the distal end of the endoscope.

In further embodiments, the array is arranged at an illumination finger, which may also be designed in a cuboid, cylinder or sphere shape. Beyond this, different micro LEDs may emit light in different emission directions. In contrast to conventional LEDs, micro LEDs, among other things, comprise a significantly smaller dimension, so that a lateral dilatation of the light-emitting surface, for example, or perpendicular to an emission direction, may comprise 500 µm at the most or less than 100 µm. The arrangement of the micro LEDs may be dense, for example, so that two adjacent micro LEDs comprise a gap as small as possible or no gap among each other, or the gap is smaller than the lateral dilatation along the connection of two adjacent micro LEDs (or is not larger than 5 times the lateral extension). In order to achieve an illumination as uniform as possible, it may be beneficial to densely arrange, in this sense, as many micro LEDs as possible, or to form groups of micro LEDs whose micro LEDs are densely arranged within a group, with the groups, however, comprising a larger distance among each other.

Thus, according to the invention, several light-emitting diodes as small as possible (as many as possible corresponding to the space conditions present) may be attached at the distal end of the endoscope or at the illumination carrier in a manner so as to optimally illuminate the endoscopically viewed scene. In this context, the micro LEDs may be fixedly fixed, shiftably, coupleable or pluggable (by means of a plug connection, for example) fixed to the illumination carrier.

Since space requirements play an important role in endoscopic applications in narrow cavities, a miniaturized design in the form of micro LEDs is of considerable importance. Using miniaturized designs allows a space-saving arrangement on the one hand, and, on the other hand, the attachment of a larger number of micro LEDs with comparable space requirements. This is of crucial importance with regard to the achievable uniformity of the illumination. Additionally, micro LEDs with different colors and/or emission directions may be arranged on the carrier.

In order to optimally realize the miniaturization, the micro LEDs according to embodiments of the invention may be attached directly as a chip, entirely without any commercial housings with standardized designs. For this purpose, the tiny micro LED semiconductor chips with a size on the order of a few micrometers to a few 100 µm are deposited onto a carrier foil (e.g. flexible or pre-shaped and with a thickness of a few micrometers) which at the same time may realize the electrical connection, by means of joint techniques such as solder joints or glued joints. The carrier foil itself is in turn deposited onto the mechanically supporting structure of the endoscope tube or an additional illumination carrier. The illumination carrier may be, for example, "a plug-on tube" shifted across the actual endoscope tube or a light finger shifted through an instrument channel of the endoscope. The carrier foil may be formed, for example, as a flexible membrane (flexible circuit board), and beyond this, may comprise a transparent material. This is particularly advantageous if the carrier is transparent, too. A pre-shaped design of the carrier foil is particularly advantageous if, for example, the illumination carrier or the endoscope comprises a strong curvature, so that a damage to the foil or to the micro LEDs might occur if a carrier foil not-preshaped was used.

For beam shaping, micro lenses for light bundling or diffuser elements for light dispersing may be attached in front of individual, a part of or all LED chips (micro LEDs), if necessary. With a paint or another transparent suitable compound, the components may protected against damage (e.g. mechanical as a result of collisions or chemical as a result of aggressive liquids). If the compound has suitable opaque, optical properties, it may serve at the same time as a diffuser or a bundling element. By means of the compound, further a smooth outer surface may be generated.

A further possibility with a smaller miniaturization degree is attaching the micro LEDs in commercial, yet miniaturized housing designs, such as SMD housings (SMD=surface mounted device, i.e. a miniaturized housing design for electronics components), which may reach up to the sub-millimeter range. For this purpose, the SMD housings of the LEDs are attached by means of suitable joint techniques, such as solder joints or glue joints.

BRIEF DESCRIPTION OF THE DRAWINGS

Embodiments of the present invention will be detailed subsequently referring to appended drawings, in which.

DETAILED DESCRIPTION

Figure 1A:
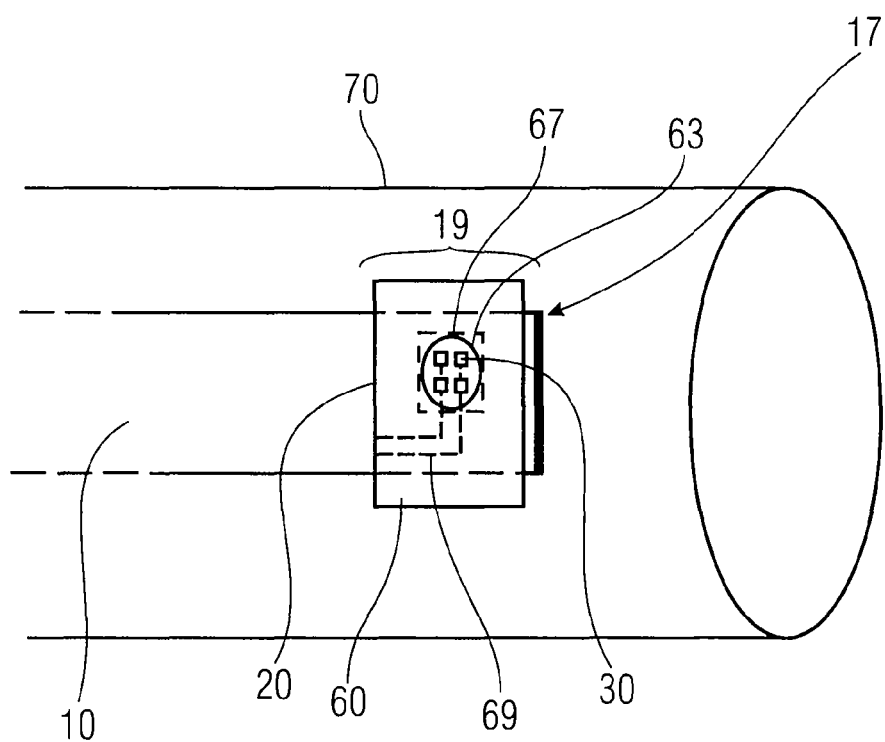
FIG. 1a is an illumination carrier (carrier) with an array-shaped arrangement of micro LEDs according to an embodiment of the present invention.
Figure 1:
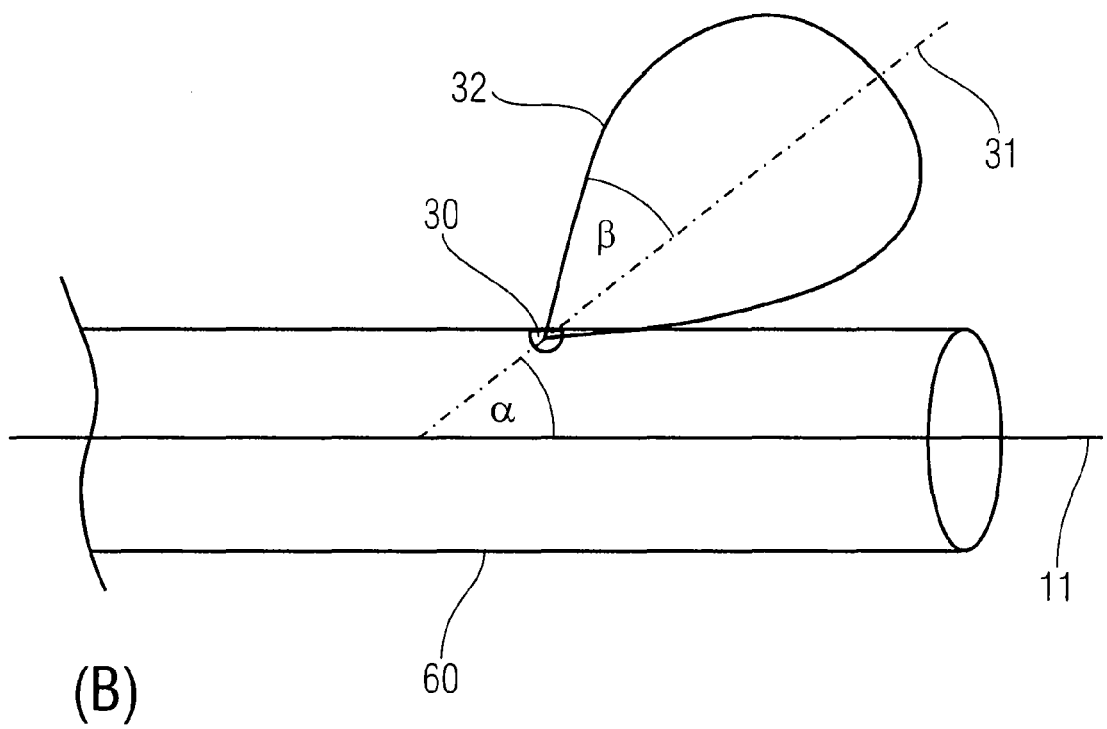
FIG. 1b-d is a micro LED at a carrier, with a lens and a diffuser.
Figure 1:
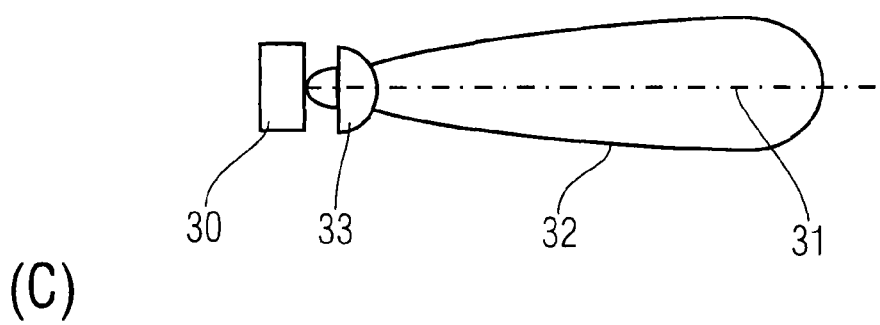
Figure 1:
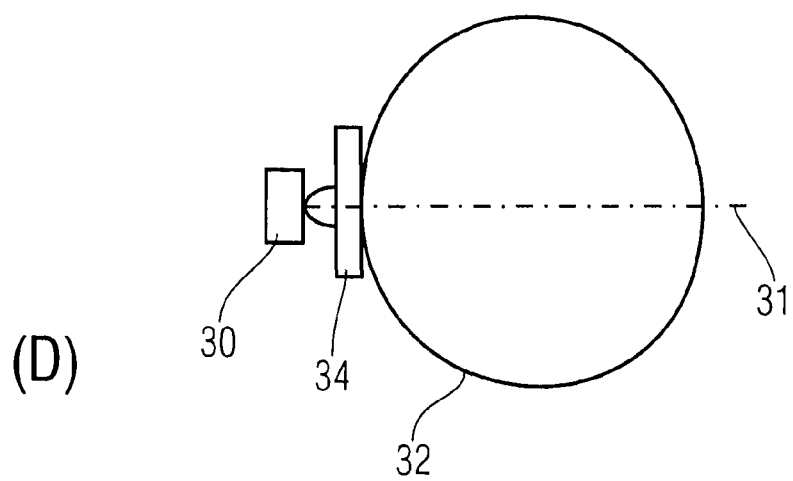

Before the present invention will be detailed subsequently referring to the drawings, it should be understood that same elements or elements acting in the same way are provided with same or similar reference numerals in the figures and that a repeated description of these elements is omitted, or explanations of these elements in different figures are correspondingly to be applied to one another or are interchangeable.

FIG. 1a shows an illumination apparatus 19 for an image sensing means 17 at the distal end 20 of an endoscope 10 with an illumination carrier 60 and a plurality of micro LEDs 30 at the illumination carrier 60 with a main surface from which the emission is made and which comprises a maximum lateral dilatation of less than 500 µm. The micro LEDs 30 are arranged at the illumination carrier 60 such that with electrical excitation, an environment of the distal end 20 of the endoscope 10 (e.g. the internal of a tube 70) is at least in some portions illuminated. For example, in the image sensing means 17, the optical sensing of the image is made by means of an optics with an objective, for example. For this purpose, the image sensing means 17 may comprise fiber glass (for optically forwarding an image) or relay lenses, too, for example. Endoscope 10 may further be designed as a videoscope so that an electrical or electronical conversion of the optical image may already take place at the distal end 20.

The plurality of micro LEDs 30 may be arranged as an array 63 or in a line-shape at an outer area of the illumination carrier 60, and the illumination carrier 60 may comprise at least 10 micro LEDs 30. In embodiments of the present invention, the main surface, or emission surface, comprises a maximum lateral dilatation of less than 300 µm, 100 µm or 10 µm and/or the main surface of a micro LED 30 comprises an area of 0.01 mm$^2$ at the most. According to embodiments of the present invention, the illumination carrier 60 may be mechanically connectable to the distal end 20 of the endoscope 10 (e.g. coupleable) and/or be shiftably arranged thereon, wherein the illumination carrier 60 may also be formed by a portion of the endoscope 10 at the distal end 20 thereof.

Tube 70 may also be part of a bore comprising only one opening into which the endoscope 10 may be introduced. The micro LEDs 30 may further be also arranged on a foil carrier 67 with conductor traces 69 serving for electrically contacting the micro LEDs 30 (energy supply).

FIG. 1b shows a carrier 60 for a micro LED 30 which is annularly arranged around a geometrical axis 11 of an optics of an endoscope 10. The geometrical axis 11 (or device axis) may also match with the optical axis of an objective (e.g. for rigid endoscopes). On the other hand, for flexible endoscopes deflecting the image field (e.g. by means of a prism or a lens, or several lenses), for example, the optical axis may differ from the geometrical axis 11. The micro LED 30 comprises a emission direction 31, and the emission is made in a particular emission characteristic 32. The emission direction 31 in this context comprises an angle α (to the optical axis 21 or to the main surface of the micro LED 30 from which the emission is made. The emission characteristic 32 is described by an opening angle β, for example, indicating in which direction region the micro LED 30 mainly emits (e.g. the region in which the micro LED 30 emits at least 70% of the light intensity). The emission direction 31 may be influenced by an optics (e.g. by a mirror) or a variation of the shape of the main surfaces and/or the refractive index difference between the main surface and an adjoining medium, for example. Additionally, the micro LEDs 30 may be arranged on the carrier in a tilted manner. The emission characteristic 32 may be changed by the micro LED 30 additionally comprising a lens, or a disperser (diffuser), for example.

FIGS. 1c-d show an illustration how the illumination characteristic 32 may be changed by a micro lens 33 or a diffuser 34. In FIG. 1c, a micro LED 30 comprising a micro lens 33 is shown, so that the illumination characteristics 32 comprises a smaller angle value β. Thus, an enhanced emission towards axis 31 occurs (focusing). In further embodiments, a lens is arranged over several micro LEDs 30, so that light of several micro LEDs 30 is bundled. Additionally, all or only part of the micro LEDs 30 may each comprise a micro lens 33. FIG. 1d shows the micro LED 30 with a diffuser 34, so that the emission characteristic 32 comprises a larger angle value for β. Thus, light is increasingly emitted away from the axis 31, and thus, an illumination of a wider visual field region is made. Here, too, a diffuser may include several micro LEDs 30, or part of or all of the micro LEDs 30 may each comprise a diffuser 34.

In embodiments of the present invention, a plurality of micro LEDs 30 is used for illumination. For distinguishing different micro LEDs 30 which may emit in different directions 31 and, beyond this, may comprise different emission characteristics 32, the following notation is used. Reference numeral aa.b.i in the following refers to a micro LED if aa=30, a emission direction if aa=31, and a emission characteristic if aa=32. In this context, the emission characteristic 32 refers to a focused emission, for example, e.g. as a result of a micro lens deposited on the micro LED 30 (see FIG. 1c) or to a diffuse emission, e.g. if a diffuser 34 is deposited on the micro LED 30 (see FIG. 1d). The emission direction 31 in this context refers to the direction in which the light intensity of the micro LED 30 comprises a maximum. The value b numbers different emission directions 31 of the micro LEDs 30 with respect to the surface of carrier 60. Finally, value i constitutes a numbering of micro LEDs 30 comprising the same emission direction 31.

Different emission directions 31 in this context refer to different angles $\alpha$ between the emission direction and the surface of carrier 60. Next to emission directions parallel to the optical axis 21 ($\alpha=0$, 180°), the angle $\alpha$ (may be larger than 15° or larger than 25°. For the instance in which five emission directions 31 are present, the different emission directions 31 may be numbered from 1 to 5, for example, so that b=1 refers to a emission direction 31 parallel to the optical axis 21 away from the distal end 20 (which may comprise an optics) of the endoscope 10 ($\alpha=0°$), a emission direction 31 with the value b=3 refers to a emission direction 31 perpendicular to the optical axis 21 ($\alpha=90°$), and a emission direction 31 with the value b=5 refers to a emission direction 31 parallel to the optical axis 21, namely a emission direction 31 facing the distal end 20 of the endoscope 10 ($\alpha=180°$). Accordingly, a emission direction 32 for the value b=2 refers to a direction for which the angle $\alpha$ comprises a value between 0° and 90° (or between 10° and 90°, 30° and 60°, 40° and 50°) (e.g. $\alpha=45°$), and b=4 refers to a direction for which the angle $\alpha$ comprises a value between 90° and 180° (e.g. $\alpha=135°$). In the values indicated here, a tolerance of +/−10° may occur, or, generally, the angles may be adapted corresponding to a desired angle of view. In each emission direction 31, several micro LEDs 30 may emit, at least 5 or 10 micro LEDs 30 per emission direction 31, for example, which may be selected differently for each emission direction 31.

In further embodiments, the micro LEDs 30 are arranged in more than five emission directions 31. In a case with n further emission directions 31 (in addition to the forward direction, $\alpha=0$), the emission directions 31 may be selected such that the difference $\Delta\alpha$ between two adjacent emission directions is 180°/n, for example. On the other hand, the emission directions 31 may also be flexibly adapted to the requirements.

Figure 2:
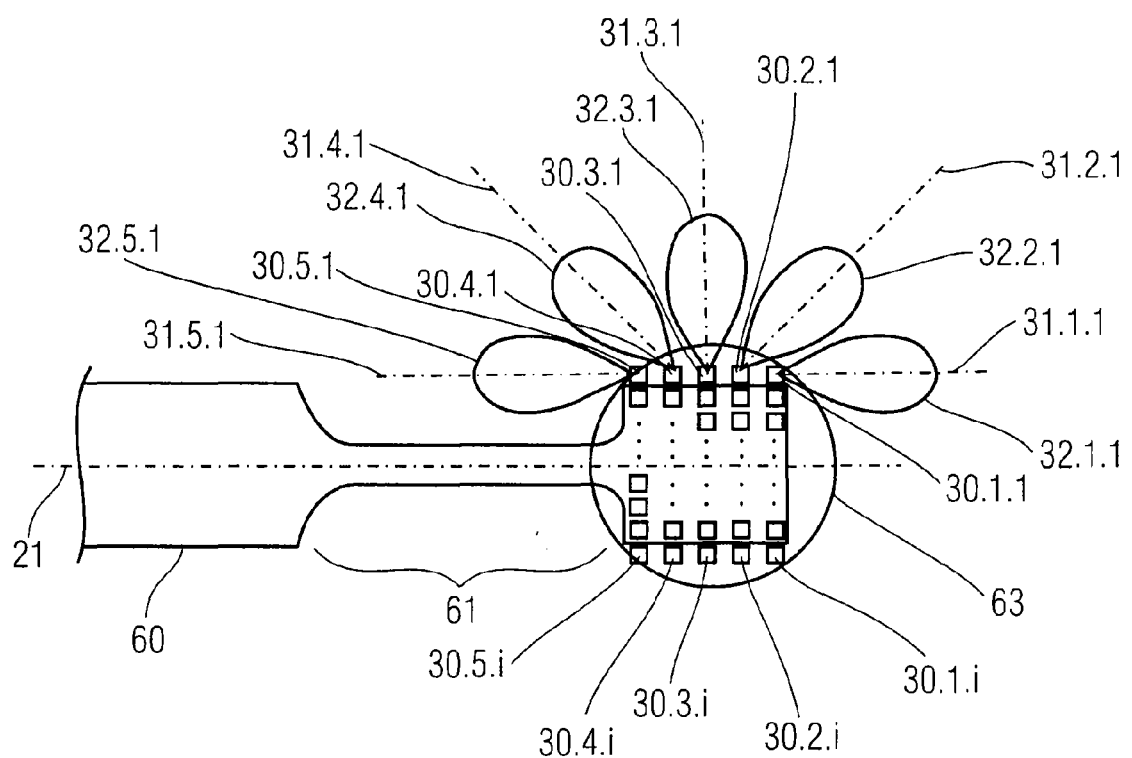
FIG. 2 is a carrier with an array-shaped arrangement of micro LEDs according to a further embodiment.

FIG. 2 shows a carrier 60 with an array-shaped arrangement 63 of micro LEDs 30 emitting in different directions. Specifically, the micro LEDs 30 comprise five emission directions for the values b=1, 2, 3, 4, 5. The value b=1 in this context corresponds to an angle $\alpha=0$, for example, the value b=2 corresponds to a value $\alpha=45°$, the value b=3 corresponds to a value $\alpha=90°$, the value b=4 corresponds to a value $\alpha=135°$, and the value b=5 corresponds to a value $\alpha=180°$, wherein the indications for the angle $\alpha$ (may comprise a tolerance of ±20%, for example. In an annular arrangement around the optical axis 21, a plurality of micro LEDs 30.b.i is arranged on carrier 60 in FIG. 2, with b=1, 2, 3, 4, 5 and i=1, 2 . . . , n illustrating a numbering of the micro LEDs 30 (n=the number of the micro LEDs 30).

Carrier 60 of FIG. 2 further comprises an opening region 61 formed such that an image sensing is possible via the opening region 61 via an optics of the endoscope 10 if carrier 60 is shifted onto an endoscope or endoscope end 10. Here, the optics may serve, for example, to project the image onto an image sensing means (a photo or video camera, CCD camera) or to transfer the optical image from the distal end to the proximal end (e.g. by means of a lens system or a light guide).

Here, the illumination carrier 60 may be connected to the endoscope 10 via a plug connection by using a plug which at the same time may provide the electrical leads. On the other hand, the illumination carrier 60 may also be electrically (by means of servo motors, for example) or mechanically shiftably arranged at the endoscope 10. Finally, the illumination carrier 60 may be fixedly connected to the endoscope 10 (e.g. by means of a glue joint).

The emission characteristic 32 of the illumination may be adapted to a direction of sight of the endoscope 10 as well as to an examination task (application area) by a different orientation of the micro LEDs 30 (LED chips), for example. For example, by separately switching on and off the corresponding micro LEDs 30, those micro LEDs emitting forwards (b=1), transversely to the side (b=2), to the side (b=3), transversely backwards (b=4) or backwards (b=5) may be activated. Beyond this, any reasonable combinations of emission directions 31 are also possible. The micro LEDs 30 illustrated in FIG. 2 are drawn by way of example only. Both the number and a packaging density may be chosen as large as possible corresponding to existing space conditions to thereby form the illumination of the environment as optimally as possible, for example, at least 10, 20, 50 or 60 micro LEDs 30 may be arranged on an illumination carrier 60. If the illumination carrier 60 (e.g. a light finger) comprises a circumference of a diameter of 2 mm, approximately 60 micro LEDs 30 with a dimension of 100 µm each may be attached.

Figure 3:
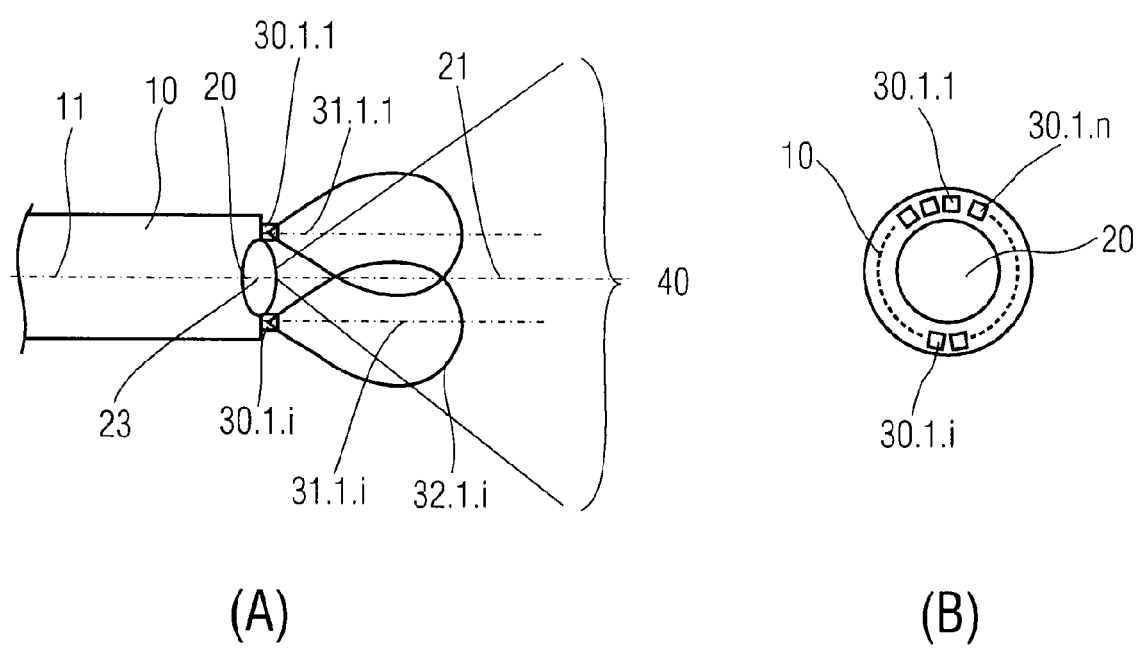
FIG. 3 is a line-shaped arrangement of micro LEDs at a distal end of an endoscope.

FIG. 3 shows a line-shaped arrangement of micro LEDs 30 around the distal end 20, which may comprise an objective 23, for example, wherein in this embodiment, all micro LEDs 30 emit in a forward direction (b=1). With a forward look, the optical axis 21 of the objective is identical with the mechanical axis 11 of the endoscope tube 10 at the distal end 20.

At the distal end 20 of the endoscope 10, forward-emitting micro LEDs 30.1.1 to 30.1.$n$ with the emission direction 31.1 as well as the intensity distributions 32.1 are annularly attached around the objective 23 in a dense packaging, illuminating the viewable visual field 40. On the one hand, it is the significantly higher miniaturization degree that is advantageous, so that substantially smaller, thinner devices suitable for examination of very small cavities, too, may also be realized. On the other hand, an arrangement with a relatively large number of micro LEDs 30 of more than 10 may thereby be realized. Thus, at the distal end 20, around the objective 23 of a 3 mm endoscope 10, approximately 50-60 micro LED chips 30 may be placed. Thereby, a significantly improved quality of illumination may be achieved, and by individually controlling single micro LEDs 30 or groups of micro LEDs (e.g. of different colors), a large number of different illumination modalities (bright, dark, different-color, etc.) may be realized.

Figure 4:
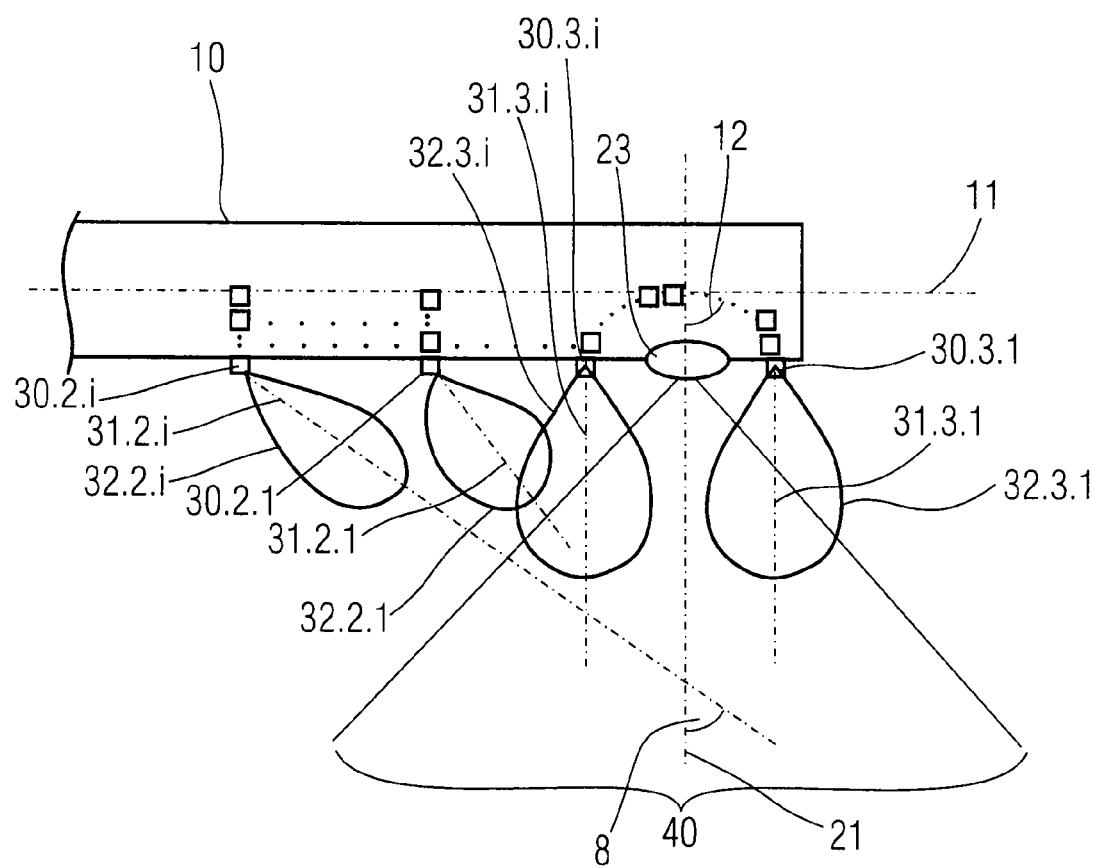
FIG. 4 is a lateral arrangement of micro LEDs at an endoscope.

FIG. 4 shows an arrangement of micro LEDs laterally arranged at an endoscope tube 10, so that illumination is provided for a laterally arranged objective 23 of the endoscope 10 with a visual field 40. In the case of a side look, the optical axis 21 of the objective 23 forms an angle 12 with the mechanical axis 11 of the endoscope tube 10 at the distal end. With the sum of the angle 12 and the angle $\alpha$, an angle $\gamma$ may be formed, for example, representing the angle between the optical axis 21 and the emission direction 31, and the optical axis 21 may be directed forwards, to the side, or transversely backwards. The angle 12 and the angle γ may thus comprise a value between 0° (forwards) and +/−160° (backwards).

In this embodiment, the micro LEDs 30 are attached in different groups, 30.2.1-30.2.$i$ to 30.3.1-30.3.$j$ distinguishing themselves by different emission directions 31.2.1-31.2.$i$ to 31.3.1-31.3.$j$ and each illuminating the observable visual field 40. The different micro LEDs 30, or the micro LED groups, may be regulated with regard to their brightness by an individual control so that different illumination modalities may thereby be realized. The cylindrical wall of a bore or a cavity may thus be illuminated in an optimum bright field or dark field arrangement, only by switching the luminous intensity of the different micro LEDs 30, or the micro LED groups.

Figure 5:
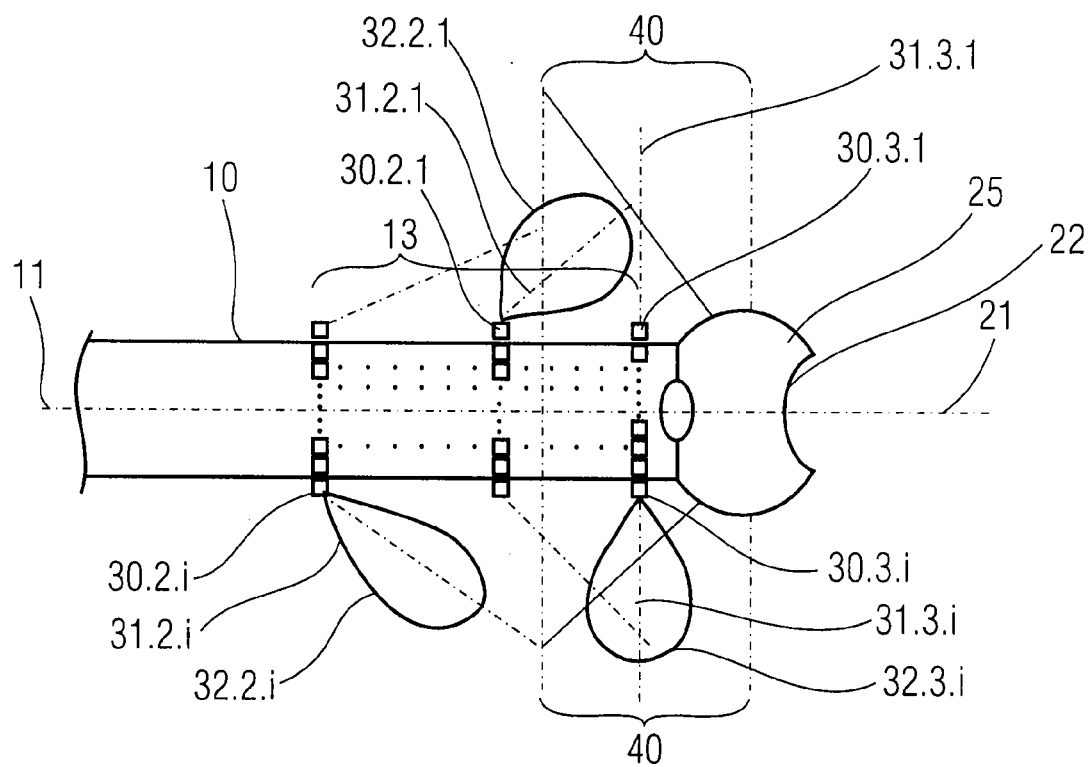
FIG. 5 is a so-called all-round backward look for an endoscope with micro LEDs at least one side wall.

FIG. 5 shows an embodiment of the present invention, wherein at the distal end 20 of the endoscope 10, a lens 25 allowing an all-round backward look or an all-round image sensing (this is possible with a so-called Greguss lens or a cone mirror, for example) is present, and the endoscope tube 10 comprises an array-shape arrangement of micro LEDs 30 at the outer wall in a region 13, wherein in this embodiment, different emission directions 31 were selected for different micro LEDs 30. For example, these may be the emission directions b=2, b=3. With an all-round backward look, the optical axis 21 of lens 25 (e.g. "Greguss lens") is identical with the mechanical axis 11 of the endoscope tube 10 at the distal end. By a front mirror 22, the observable visual field 40 is redirected such that an all-round look is made laterally or transversely backwards, but no forward look is possible.

The micro LEDs 30 are attached in different groups, 30.2.1-30.2.$i$ to 30.3.1-30.3.$j$ comprising different emission directions 31.2.1-31.2.$i$ to 31.3.1-31-3-$j$ and each illuminating the observable visual field 40. The different micro LEDs 30, or the micro LED groups, may be regulated with regard to their brightness by an individual control, so that different illumination modalities may thereby be realized. The cylindrical wall of a bore or a cavity may thus be illuminated in an optimum bright field or dark field arrangement, by switching the luminous intensity of the different micro LEDs 30, or the micro LED groups.

Figure 6:
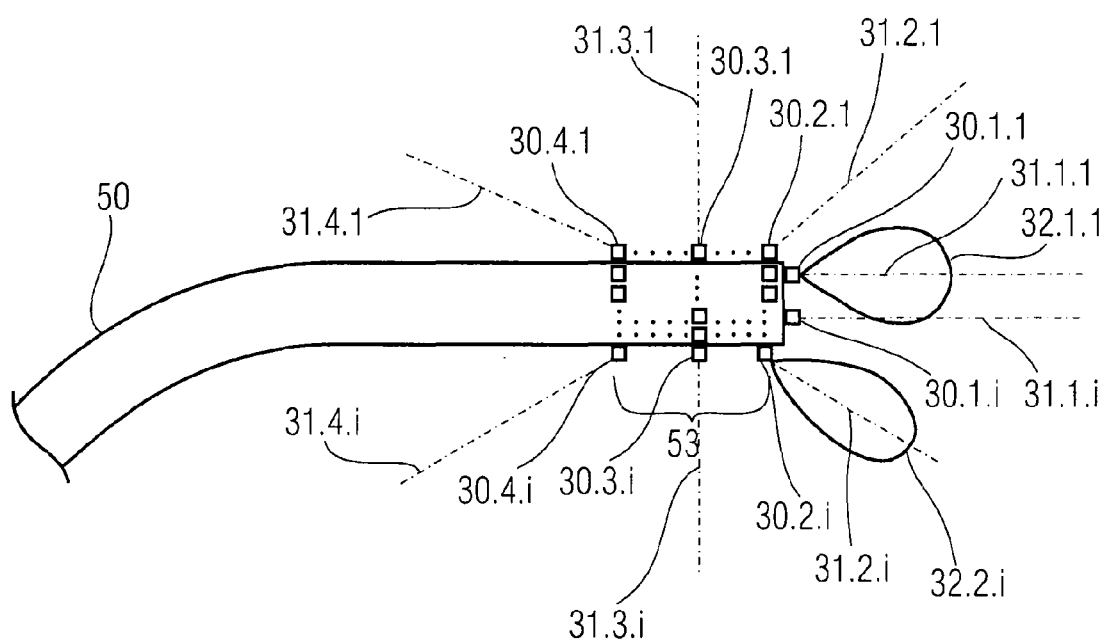
FIG. 6 is a rod-shaped carrier for micro LEDs.

FIG. 6 shows an embodiment in which an array-shaped arrangement of micro LEDs 30 is arranged in a region 53 of a light finger 50. The light finger 50 is an example for a separate illumination carrier in which the micro LEDs 30 are arranged substantially cylindrically to the endoscope tube 10 in an analog manner. Here, the emission directions 31 for different micro LEDs 30 in this embodiment of FIG. 6 are 31.1, 31.2, 31.3 and 31.4. In further embodiments, however, still further directions or combinations are possible.

The light finger 50 may be shaped such that it may be advanced through an instrument channel 52 of the endoscope 10 from the proximal to the distal end 10 (not shown in FIG. 6), and there it exists. Here, the rigid or flexible rod-shaped (cylindrical) body formed as light finger 50 carries the micro LEDs 30 at the distal tip.

Figure 7:
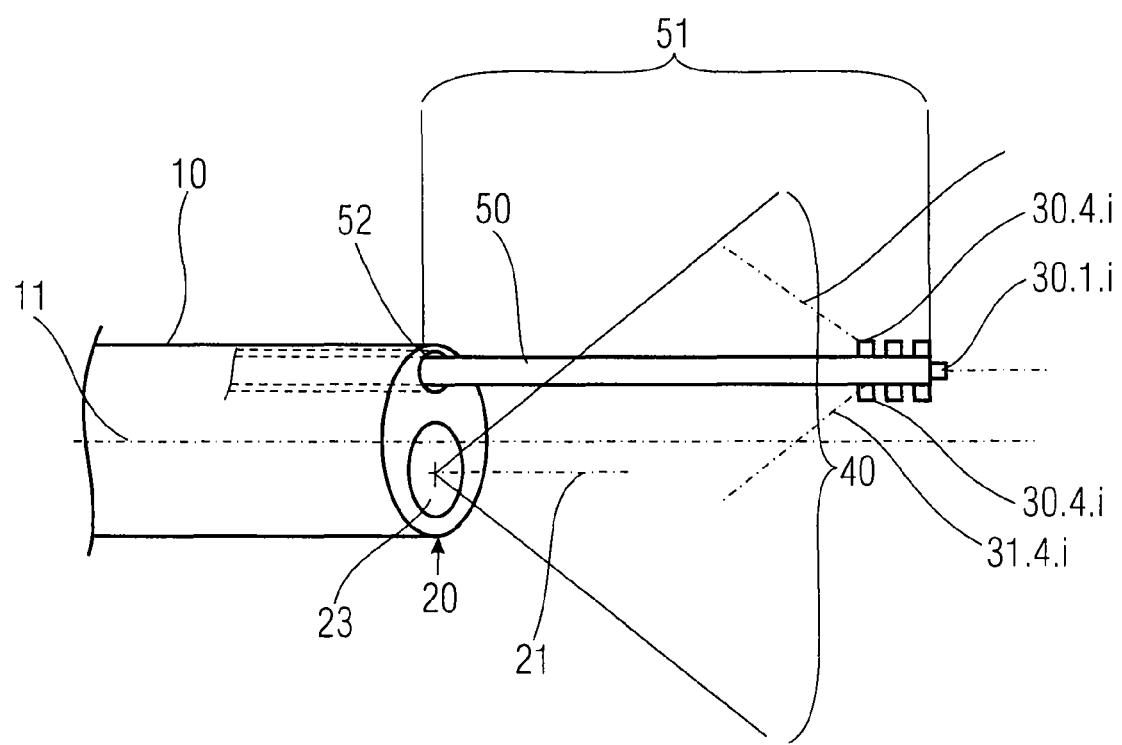
FIG. 7 is an endoscope with a moveable rod-shaped carrier for micro LEDs.

FIG. 7 shows an embodiment in which the micro LEDs 30, as shown in FIG. 6, are arranged on a light finger 50, wherein the light finger 50 is movably attached in an instrument channel 52 of the endoscope 10, and wherein different regions may be illuminated by shifting the light finger 50 in and out, for example. In this embodiment, the endoscope 10 comprises an objective 23 with a visual field 40 at the distal end 20, wherein the optical axis 21 is shifted from the geometrical axis 11.

Thus, a realization of a bright field illumination of cylindrical bore walls is possible in a backlight arrangement, wherein the light finger 50 is shifted forwards by a certain extent 51 to the front of the tip of the endoscope 10 for this purpose, so that a bright field illumination is realized by activating the micro LEDs 30 emitting backwards (directions 31.3-31.5). Here, by a variation of the extent 51, the illumination quality may be further influenced and optimized. The hiding effects inevitably occurring with the advanced light finger 50 may be compensated for by a rotation between shifting the endoscope 10 in and out, for example.

Figure 8:
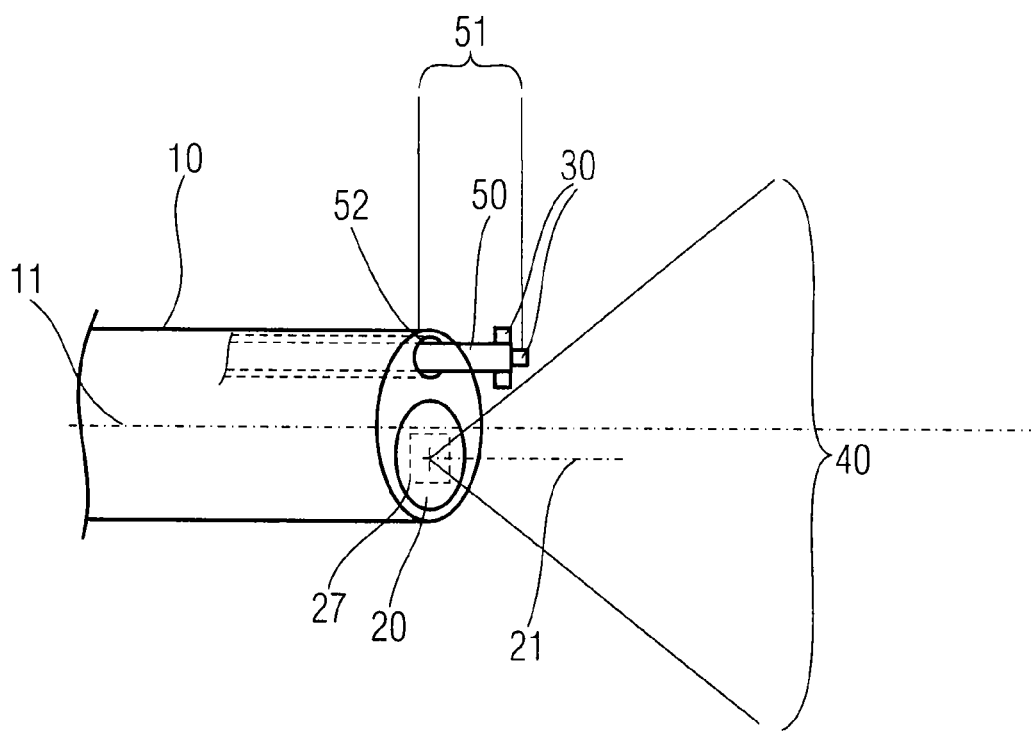
FIG. 8 is an endoscope with a moveable rod-shaped carrier for micro LEDs outside the visual field of the optics.

FIG. 8 shows an embodiment in which the endoscope 10 comprises a movable light finger 50 with micro LEDs 30 as in FIG. 7, wherein in the embodiment shown in FIG. 8, the light finger 50 has been shifted into the instrument channel 52 of the endoscope 10 so far that the visual region 40 of the objective 23 of the endoscope 10 is not limited by the light finger 50. Here, the light finger 50 may be withdrawn so far that the extent 51 becomes so small that no hiding effects occur in the observable visual field 40. If the micro LEDs 30 emitting forwards (31.1-31.3) are activated, a bright field illumination in an incident light arrangement may be realized for the base of a sack bore.

Figure 9:
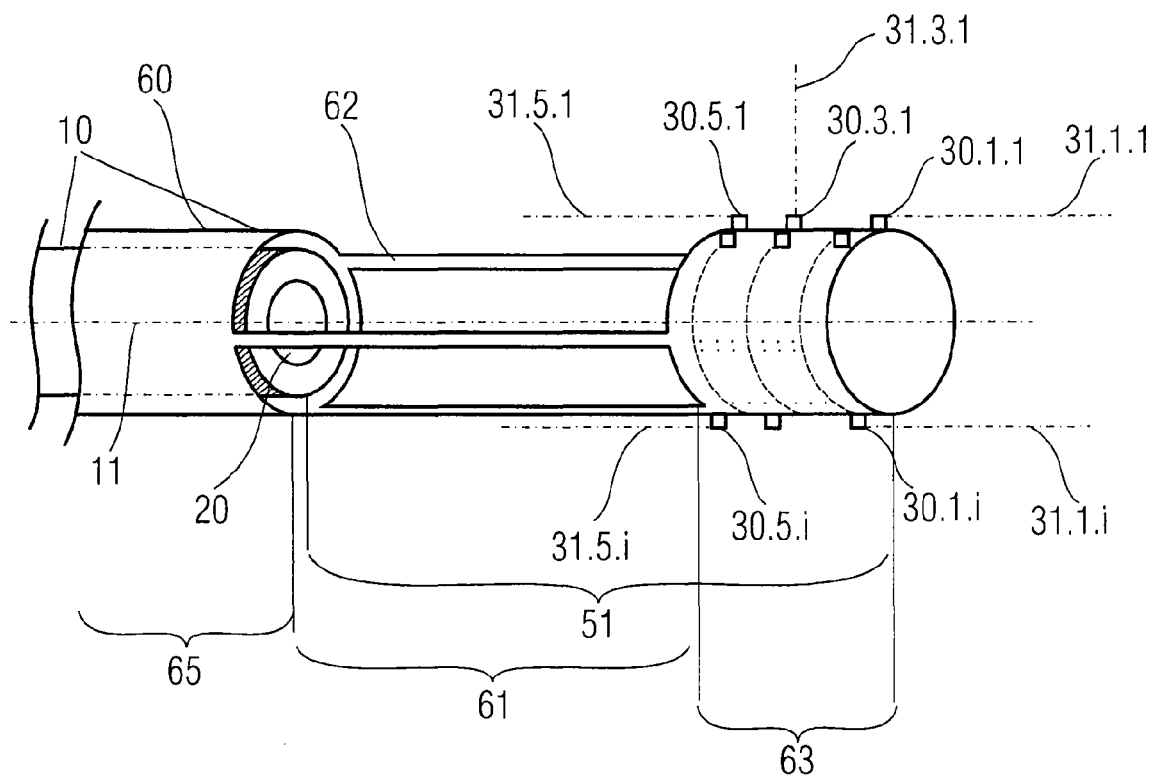
FIG. 9 is a carrier for micro LEDs at the distal end of the endoscope with lateral windows.

FIG. 9 shows an embodiment in which carrier 60 for the micro LEDs 30 is formed as a thin-walled tube comprising a window region 61. The window region 61 thus allows the objective 23 at the distal end 20 of the endoscope 10 to sense the illuminated surrounding. In this embodiment, the geometrical axis 11 matches the optical axis 21. The micro LEDs 30 may be attached with the emission directions 31.1 to 31.5 or in any combinations of these directions. Tube 60 is shaped such that it may be fittingly shifted over the distal end 20 of the endoscope 10. The (plug-on) tube 60 is divided into three regions, wherein the window region 61 separates a region 63 comprising the micro LEDs 30 from a support region 65 shifted onto the endoscope 10. Thus, extent 51 of FIG. 7 and FIG. 8 includes the window region 61 and the region 63. The window region 61 comprises large windows across the entire circumference into the tube 60, for example, so that only narrow ribs 62 remain in the window region 61, and, thus, a largely unhindered look 40 is possible from the inside of the plug-on tube to the outside. The electrical supply of the micro LEDs 30 may be led along the ribs 62. Optionally, both the support region 65 and the ribs 62 may comprise further micro LEDs 30, which may also emit in different emission directions 31, that is, which may be arranged, or formed, according to all embodiments described.

For realization of a bright field illumination of cylindrical bore walls in a backlight arrangement, the plug-on tube 60 is shifted forwards by a certain extent 51 to the front of the tip of the endoscope 10, so that by activating the micro LEDs 30 emitting backwards (31.3-31.5), a bright field illumination is realized. Here, by a variation of the extent 51, the illumination quality may further be influenced and optimized. The hiding effects inevitably occurring with the plug-on tube shifted forwards may be compensated for by one or several rotations, as already described.

If the micro LEDs 30 emitting forwards (31.1-31.3) are activated, a bright field illumination in an incident light arrangement may be realized for the base of a sack bore. In this context, the plug-on tube 60 may be withdrawn such that the extent 51 becomes so small that no hiding effects occur in the observable visual field 40.

Figure 10:
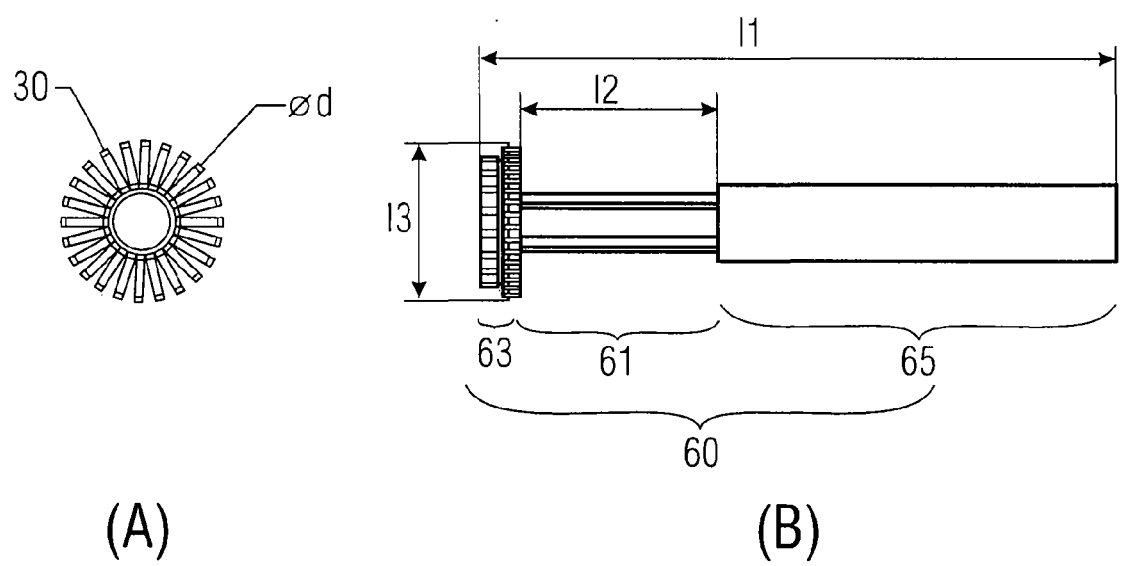
FIG. 10 shows images of an arrangement of micro LEDs with and without a diffuser.

FIG. 10 shows an embodiment in which an annular arrangement of micro LEDs 30 comprises a diffuser 34. In this context, FIG. 10$a$ shows a front view of an arrangement of 33 micro LEDs 30 annularly arranged around a circle with a diameter d. FIG. 10$b$ shows a side view of a carrier 60 comprising the annular arrangement of the micro LEDs 30 at an end 63, as shown in FIG. 10$a$. The embodiment of FIG. 10$b$ further comprises a window region 61 allowing image sensing by an endoscope 10 shifted into the carrier 60 in the region 65. Exemplary dimensions include a total length l1 of approximately 64 mm for carrier 60, a length l2 of approximately 20 mm for the opening region 61, and of approximately 15.7 mm for a diameter 13 of the annular arrangement of the micro LEDs 30, wherein these dimensions may comprise a tolerance of +/−50%.

Figure 10C:
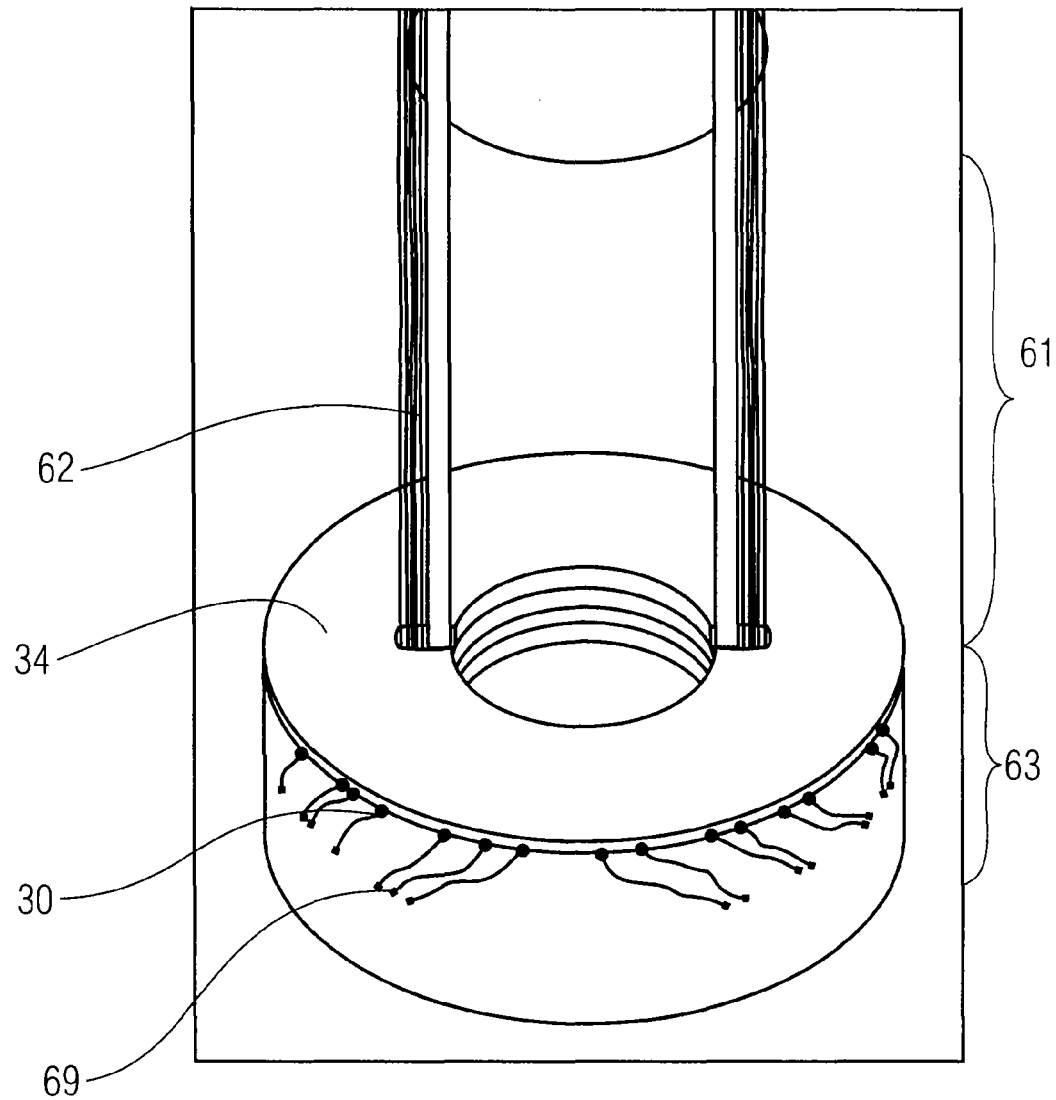
Figure 10D:
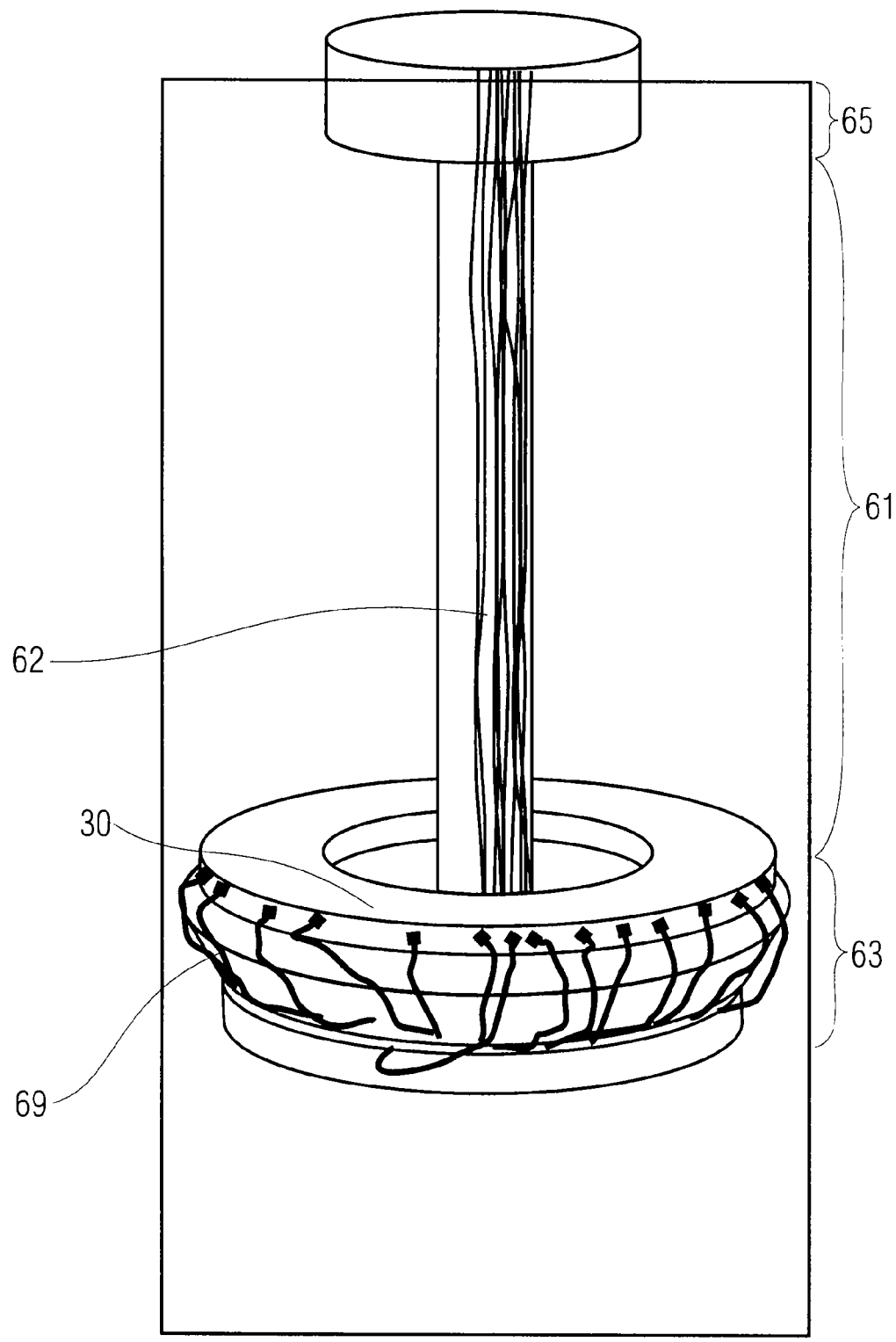

For example, the plug-on tube 60 may altogether comprise 52 micro LEDs 30 in two emission directions, e.g. forwards (31.1) and backwards (31.5), wherein the number of micro LEDs 30 may vary for each emission direction. The plug-on tube 60 comprises an internal diameter d of approximately 6.6 mm, fitting for a 6.5 mm endoscope. For both emission directions 31, a diffusion disk (diffuser 34) is each attached in front of the micro LEDs 30. FIG. 10c, d show illustrations with and without diffuser elements 34.

Figure 11:
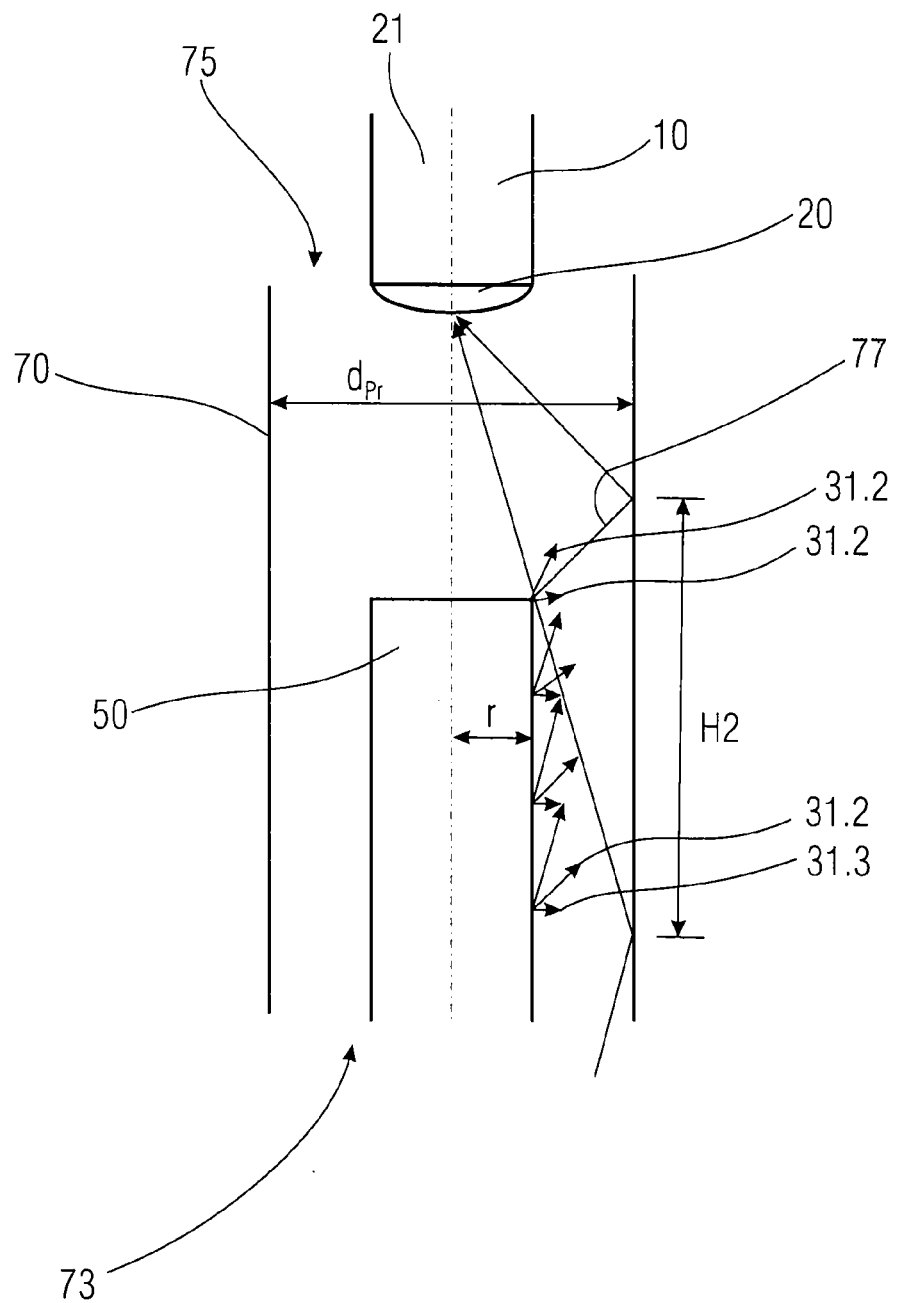
FIG. 11 is an illumination region of a carrier with an array of micro LEDs.

FIG. 11 shows an embodiment in which a cavity inside a tube 70 comprising a first opening 73 and a second opening 75 is to be examined with an endoscope 10. For this purpose, carrier 50 with the micro LEDs 30 (not shown in FIG. 11) is introduced into the cavity from the first opening 73. Carrier 50 comprises a radial diameter r and has, at the outer wall, micro LEDs 30 emitting in different directions, such as 31.2 and 31.3. Via reflections at the inside wall of tube 70, the light beams 77 enter the objective 23 of the endoscope 10. The diameter of tube 70 is $d_{Pr}$, and the optical axis 21 is here laid along the center of tube 70. Here, an illuminated field is designated H2, wherein the distance H2 may be larger than $d_{Pr}$, for example. In this context, an advantage of the present invention is in particular that the illumination region H2 may be chosen significantly larger by different emission directions 31.b than it would be the case for only one predetermined emission direction 31.

In further embodiments, an electronical image sensing is made directly at the distal end 20 of the endoscope 10 (e.g. by a CCD camera) or the image is sensed by optical means (e.g. by means of an objective, lenses, etc.) and forwarded to the proximal end where an image sensing is also possible. In this context, forwarding may also be made by means of a light guide, for example.

To summarize, the inventive use of micro LEDs 30 thus offers the most various possibilities of deployment and is advantageous for the automated endoscopy in particular. For example, the sidewall as well as the base of the bore 70 may be completely sensed with a single inspection ("driving in") of an exemplary sack bore with an optimum illumination. For sensing the wall, the plug-on tube, or the light finger 50, is in a forward-shifted position, and the micro LEDs 30 emitting (transversely) backwards are turned on: The bore wall is illuminated in a bright field arrangement and captured. At the end of the sack bore, the plug-on tube, or the light finger 50, is withdrawn until the look at the base of the bore is unhindered, and the micro LEDs 30 emitting forwards are turned on, and the base of the bore may be sensed.

For many applications, using micro LEDs 30 in different colors (for example, united into groups) is advantageous (since certain structures are particularly clear in certain colors, for example). Additionally, the area emission by means of arrays offers the advantage that a uniform illumination of larger regions may be achieved. By separately switching on and off certain groups of micro LEDs 30 (optionally also in different colors), certain regions may be further specifically illuminated. Finally, a pulsed operation may be reasonable for an automatic image recognition to avoid motion blurs, for example. Here, the pulsed control may relate to all micro LEDs 30 or only to a part of the micro LEDs.

Further advantages of inventive embodiments may be summarized as follows.

By the small size of the LED chips, the micro lenses 33 or diffusers 34 as well as electrical leads 69 on the order of a few micrometers to a few 100 μm (e.g. from 1 μm to 500 μm or 3 μm to 200 μm), an extremely space-saving construction with a volume smaller than with light-guiding glass fibers or comparable may be made (particularly important for very small cavities, substantially smaller than approximately 5-10 mm, to be examined with thin endoscopes). For example, the micro LEDs 30 may comprise a maximum dilatation of a main surface, from which the emission is made, of less than 500 μm, 300 μm or 100 μm and, for example, 1-20 μm with respect to an edge length or a diagonal. The micro LEDs 30 may be, for example, cuboid-shaped, cube-shaped, or may also comprise an oblong shape, wherein all or part of the side areas may comprise the maximum lateral dilatation.

In particular, inventive embodiments thus allow an arrangement with much more than four LEDs, for example, at the distal end of the endoscope, which may annularly arranged around the pupil of the objective, for example. Thus, due to the small dimensions of the micro LEDs 30, inventive embodiments may be also used for small bores with a diameter of 10 mm or less. It is also possible to provide the working tip of the endoscope 10 with a matrix of small, superbright LEDs in an SMD design.

Due to their small size, the micro LEDs 30 may be attached in almost any orientation at the distal end 20 of the endoscope 10, so that most various illumination characteristics may be realized depending on the application.

Due to their small size, the micro LEDs 30 may also be attached in several different orientations at the distal end 20 of the endoscope 10, so that different illumination characteristics may be realized during an inspection in a simple manner by electrically switching or dimming the different micro LEDs 30 or micro LED groups.

By attaching many micro LEDs 30 distributed across a certain region of the endoscope shaft or the external illumination carrier 50, a larger region of the inner surface (of the cavity to be examined) may be optimally illuminated, so that an inspection may be made faster. Thereby, shifting the illumination carrier 50 or the endoscope 10 to and fro may be avoided.

By the light generation directly at the distal end 20 of the endoscope 10, light transmission via lossy, voluminous light guides of glass or plastic fibers is omitted.

The resulting light yield is significantly higher, so that high- or highest-efficiency LEDs are not inevitably necessary.

The energy supply with electrical energy may be made by very thin wires or thin, flexible conductor foils 67. Thereby, the micro LEDs 30 may be controlled individually or in groups from the proximal end 20 by means of controllable electrical current supplies.

Voluminous, expensive, external cold-light sources, partly with short-lived high-efficiency lamps, are omitted and may be substituted by compact current supply devices with a smaller efficiency for the micro LEDs 30.

By a control of the light intensity by the LED current which is almost free from delay, pulsed or stroboscopic illumination modalities may be realized, which is particularly of importance when recording moved image sequences by means of a camera when driving into a cavity (avoidance of motion blur).

By white, different-color or multicolored micro LED devices 30 being available, endoscopic illumination apparatuses 19 with an electrically controllable color, or variable hue, may be simply realized with a suitable combined attachment of such different micro LEDs 30. This is important in applications in which the color is the crucial examination subject (e.g. inflammatory stadium of human tissue).

Finally, by selecting the emission direction 31 (e.g. by switching in or off micro LEDs 30 with different emission directions), the above-mentioned problem of the region not sensed may be solved.

The micro LEDs 30 may be fixedly connected with the endoscope 10 or may be attached on carriers 60, 50 which are movable relative to the endoscope 10.

An illumination carrier 50, 60 may be formed in different manners, e.g. as stationary or a movable illumination carrier 60, as a plug-on tube or as a light finger 50.

With a stationary illumination carrier 60, the micro LEDs 30 may be fixedly attached at or close to the distal end 20 of the endoscope 10. In this context, different illumination modalities may be realized in a simple manner by the micro LEDs 30 with different emission directions 31 or characteristics 32 being attached and being each controlled with regard to their respective light intensity by a control means, corresponding to the specific situation/task.

A micro LED illumination on an external illumination carrier 50, 60 movable with respect to the endoscope 10 is advantageous in that the spatial arrangement of the illumination may be changed at the location, with an endoscope 10 introduced, relative to an observing objective often located at the distal end 20, and, thus, different illuminations of the cavity may be realized during a single inspection.

Using light fingers 50 as an external illumination carrier is, on the other hand, advantageous when examining through bores into which the light finger 50 may be introduced through the opposed opening of the bore independently of the endoscope 10. In contrast to commercial light fingers with a point-shaped light source at the tip, here, too, a significantly improved illumination may be achieved with the inventive micro LED illumination. With an attachment of the micro LEDs 30 in one of the lateral emission directions 31.3 over a certain region, a significantly larger region may be optimally illuminated.

With a plug-on tube, the micro LEDs 30 are attached on a tube, which is plugged over the endoscope 10, fitting the diameter of the endoscope 10, and is shiftably and rotatably supported. The micro LEDs 30 are circumferentially distributed and attached at the forward end of the tube. In the following tube portion, windows 61 as large as possible are inserted into the tube wall. This serves for a look at the wall of the cavity as unhindered as possible to be achieved, with a forwards-shifted tube. For example, two windows 61 and two ribs 62 may be present, holding a front ring 63 with the micro LEDs 30. The electrical leads for supplying the micro LEDs 30 may also be led along these ribs 62. Other arrangements with several ribs 62 are also possible.

A further possibility is a transparent plug-on tube, e.g. of glass or plastic. Cutting out windows 61, or ribs 62, is then not necessary. The electrical leads 69 for the micro LEDs 30 may also be deposited onto the tube in the form of transparent conductor lines, so that no circumferential hiding by ribs or electrical leads results. However, the quality of the transparent tube must satisfy high optical demands, since imaging the cavity surfaces is made through the wall of the transparent plug-on tube. The passage of the light beams through the curved surfaces of the tube wall must be taken into consideration when forming the distal objective 23.

The illuminants may also be arranged on a light finger which is shifted forwards to the distal end 20 through an instrument channel of the endoscope 10 and there exits the endoscope 10, thus, illuminating the scene.

Since, with an illumination carrier—light finger 50 or plug-on tube 60—shifted forwards, a certain portion of the bore wall is inevitably hidden in the observable visual field, the bore wall cannot be completely imaged circumferentially for 306° from one position.

For sampling the entire wall surface, the plug-on tube, the endoscope 10 or the examination part must be rotated around an angle, so that the surface regions initially hidden by the ribs 62 come to lie in the windows 61 and, thus, also become viewable. In an automatic image gain, this may be made such that a first image sequence is sensed when driving into the bore, said rotation is performed at the end of the driving-in motion, and a second image sequence now containing the surface regions previously hidden is captured when driving out of the bore. For the automated evaluation of the bore, now both image sequences may be evaluated separately and the evaluation results may be combined into an overall evaluation, or both the image sequences may initially be brought together by help of registration algorithms, so that an undistorted overall image of the inner surface results, which is then delivered to an image evaluation.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

The invention claimed is:

1. An illumination apparatus for an image sensor at a distal end of an endoscope, comprising:
    an illumination carrier which extends along a geometrical axis at the distal end of the endoscope, and
    an array of micro LEDs each comprising a main surface comprising a maximum width of less than 500 µm from which emission is made, and which are arranged on the illumination carrier such as to illuminate, with electrical excitation, at least some portions of an environment of the distal end of the endoscope; wherein
    the illumination carrier includes a support region, an opening region, and an illumination region, the opening region extending along the geometrical axis between the illumination region and the support region to form a window region extending along the geometrical axis in a lateral direction, wherein the micro LEDs are arranged at the illumination region and the support region is arranged at the distal end of the endoscope, so that an optical image of the environment at the distal end of the endoscope may be sensed through the window region in the lateral direction; and
    the illumination carrier comprises a transparent tube or a plurality of ribs arranged between the illumination region and the support region to mechanically connect the illumination region to the support region.

2. The illumination apparatus according to claim 1, wherein the array of micro LEDs is arranged on an outer area of the illumination carrier.

3. The illumination apparatus according to claim 1, wherein the illumination carrier comprises at least 10 micro LEDs.

4. The illumination apparatus according to claim 1, wherein the micro LEDs each comprise a main surface comprising a maximum width of less than 300 µm, 100 µm, 10 µm from which the emission is made.

5. The illumination apparatus according to claim 4, wherein the main surface of at least one of the micro LEDs comprises an area of 0.01 mm 2 at the most.

6. The illumination apparatus according to claim 1, wherein the illumination carrier is mechanically connectable to the distal end of the endoscope.

7. The illumination apparatus according to claim 1, wherein the illumination carrier is shiftably arranged at the distal end of the endoscope and is shiftable along the geometrical axis.

8. The illumination apparatus according to claim 1, wherein the illumination carrier is formed by a portion of the endoscope at the distal end thereof.

9. The illumination apparatus according to claim 1, wherein a first group of micro LEDs and a second group of micro LEDs are arranged on a surface of the illumination carrier, wherein the first group of micro LEDs comprises a first main emission direction and the second group of micro LEDs comprises a second main emission direction, wherein the first and the second main emission direction differ with respect to the surface region of the illumination carrier by an angle $\alpha \neq 0°$.

10. The illumination apparatus according to claim 9, wherein the first main emission direction or the second main emission direction differs from an optical axis of the image sensor at the distal end of the endoscope by an angle γ with $0° \leq \gamma \leq 160°$ or $-160° \leq \gamma \leq 0°$.

11. The illumination apparatus according to claim 1, wherein at least a portion of the micro LEDs comprise a micro lens.

12. The illumination apparatus according to claim 1, wherein at least a portion of the micro LEDs comprise a diffuser.

13. The illumination apparatus according to claim 1, wherein the illumination carrier comprises a compound arranged to protect the micro LEDs.

14. The illumination apparatus according to claim 13, wherein the compound forms a diffuser.

15. The illumination apparatus according to claim 1, wherein the illumination carrier comprises transparent glass or translucent plastic.

16. The illumination apparatus according to claim 1, wherein the micro LEDs are arranged on the illumination carrier by a carrier foil.

17. The illumination apparatus according to claim 16, wherein the carrier foil comprises conductor traces for contacting the micro LEDs.

18. The illumination apparatus according to claim 17, wherein the conductor traces are formed transparently.

19. The illumination apparatus according to claim 1, wherein at least a portion of the micro LEDs is controllable in a pulsed manner.

20. The illumination apparatus according to claim 1, wherein at least a portion of the micro LEDs are controllable separately from each other.

21. The illumination apparatus according to claim 1, wherein different micro LEDs emit light at different wavelengths.

22. The illumination apparatus according to claim 1, wherein the image sensor comprises optics with an objective at the distal end.

23. The illumination apparatus according to claim 22, wherein the image sensor comprises optics with an all-round backward look at the distal end for an all-round sensing.

24. The illumination apparatus according to claim 1, wherein the image sensor comprises a CCD camera.

25. The illumination apparatus according to claim 1, wherein the illumination carrier is implemented as a socket pipe which is at its support region shiftably arranged at the distal end of the endoscope, such that the illumination carrier is shiftable to a plurality of different illumination positions.

26. The illumination apparatus according to claim 1, wherein the illumination carrier comprises a ring-shaped illumination region.

27. The illumination apparatus according to claim 26, wherein the micro LEDs are arranged at the ring-shaped illumination region.

28. The illumination apparatus according to claim 26, wherein the illumination carrier comprises a plurality of ribs arranged to hold the ring-shaped illumination region, wherein the plurality of ribs are arranged between the ring-shaped illumination region and the support region.

29. The illumination apparatus according to claim 1, wherein the illumination region comprises a front-ring, wherein the micro LEDs are arranged at the front-ring.

30. Illumination apparatus according to claim 1, wherein the illumination carrier is rotatably arranged at the distal end of the endoscope.

31. An illumination apparatus for an image sensor at a distal end of an endoscope, comprising:
 an illumination carrier having an illumination region associated with the distal end of the endoscope; and
 an array of micro LEDs, each including a main surface comprising a maximum width of less than 500 μm from which emission is made, which are arranged on the illumination region to illuminate, with electrical excitation, at least some portions of an environment of the distal end of the endoscope; wherein
 the array of micro LEDs includes a first and a second neighboring group of micro LEDs on a surface region of the illumination region with a first and a second main emission direction which differ with respect to a direction perpendicular to the surface region of the illumination region;
 the illumination carrier includes a support region;
 the illumination carrier comprises a transparent tube or a plurality of ribs arranged between the illumination region and the support region to mechanically connect the illumination region to the support region;
 the illumination region includes a ring-shaped illumination region; and
 the transparent tube or the plurality of ribs of the illumination carrier are arranged between the ring-shaped illumination region and the support region to hold the ring-shaped illumination region.

32. An illumination apparatus for an image sensor at a distal end of an endoscope, comprising:
 an illumination carrier which extends along a geometrical axis at the distal end of the endoscope, and
 an array of micro LEDs each comprising a main surface comprising a maximum width of less than 500 μm from which emission is made, and which are arranged on the illumination carrier such as to illuminate, with electrical excitation, at least some portions of an environment of the distal end of the endoscope; wherein
 the illumination carrier includes a support region, an opening region, and an illumination region, the opening region extending along the geometrical axis between the illumination region and the support region, wherein the micro LEDs are arranged at the illumination region and the support region is arranged at the distal end of the endoscope, so that an optical image of the environment at the distal end of the endoscope may be sensed through the opening region;

the illumination carrier comprises a ring-shaped illumination region; and the illumination carrier comprises a plurality of ribs arranged to hold the ring-shaped illumination region, wherein the plurality of ribs are arranged between the ring-shaped illumination region and the support region.

33. An illumination apparatus for an image sensor at a distal end of an endoscope, comprising:

an illumination carrier which extends along a geometrical axis at the distal end of the endoscope, and an array of micro LEDs each comprising a main surface comprising a maximum width of less than 500 $\lambda$m from which emission is made, and which are arranged on the illumination carrier such as to illuminate, with electrical excitation, at least some portions of an environment of the distal end of the endoscope; wherein the illumination carrier includes a support region and an illumination region;

the micro LEDs are arranged at the illumination region and the support region is arranged at the distal end of the endoscope;

the illumination carrier is shiftably arranged at the distal end of the endoscope; and the illumination region is shiftable parallel to or along the geometrical axis to a plurality of different illumination positions with respect to the distal end of the endoscope;

the illumination region includes a ring-shaped illumination region; and the illumination carrier includes a transparent tube or a plurality of ribs arranged between the ring-shaped illumination region and the support region to hold the ring-shaped illumination region.

* * * * *

UNITED STATES PATENT AND TRADEMARK OFFICE
CERTIFICATE OF CORRECTION

PATENT NO. : 9,192,290 B2
APPLICATION NO. : 12/021481
DATED : November 24, 2015
INVENTOR(S) : Spinnler et al.

It is certified that error appears in the above-identified patent and that said Letters Patent is hereby corrected as shown below:

In the claims

Claim 4, Column 14, line 66 should be corrected as follows:

"...less than 300 μm, 100 μm, or 10 μm..."

Claim 5, Column 15, line 3 should be corrected as follows:

"...an area of 0.01 mm$^2$ at the most..."

Claim 10, Column 15, lines 27 and 28 should be corrected as follows:

"...an angle $\gamma$ with $0° \leq \gamma \leq 160°$ or $-160° \leq \gamma \leq 0°$."

Signed and Sealed this
Twenty-first Day of June, 2016

Michelle K. Lee
*Director of the United States Patent and Trademark Office*